United States Patent [19]
Ciccarello et al.

[11] Patent Number: 5,976,028
[45] Date of Patent: Nov. 2, 1999

[54] GOLF CLUB SPINE FINDER AND METHOD

[76] Inventors: Carl Ciccarello, 7 Park Ave., Glen Cove, N.Y. 11542; Iain Mossman, 168 Park Ave., Huntington, N.Y. 11743; Robert Callis, 10 951 Gulf Shore Dr., #303, Naples, Fla. 34108

[21] Appl. No.: 09/103,146

[22] Filed: Jun. 22, 1998

[51] Int. Cl.[6] .............................. A63B 57/00; G01N 3/00
[52] U.S. Cl. ....................................... 473/289; 73/862.49
[58] Field of Search .................................. 473/282, 316, 473/289, 407; 73/862.391, 862.451, 862.392, 862.49

[56] References Cited

U.S. PATENT DOCUMENTS

| | | | |
|---|---|---|---|
| 1,953,916 | 4/1934 | Adams | 73/65.03 |
| 3,992,933 | 11/1976 | Randolph . | |
| 4,517,843 | 5/1985 | Leger | 73/847 |
| 4,558,863 | 12/1985 | Haas | 473/289 |
| 4,682,504 | 7/1987 | Kobayashi | 73/854 |
| 4,958,834 | 9/1990 | Colbert | 473/289 |
| 5,379,641 | 1/1995 | Paasivaara | 473/289 |
| 5,429,008 | 7/1995 | Matsumoto . | |
| 5,515,717 | 5/1996 | White | 73/65.03 |

*Primary Examiner*—Steven Wong

[57] ABSTRACT

A golf club spine finder comprising a shaft holding member which comprises a bottom wall and a vertical member. The vertical member comprises a plurality of extended members, each extended member further comprising extended member apertures. A gripping member functions to secure the shaft holding member in a substantially upright position. A golf club shaft is then removably inserted through the extended member apertures of the shaft holding member, the golf club shaft comprising a traditional grip end and club head end. An indicator handle comprises at least one aperture further comprising roller bearings therein and a display. The golf club shaft is removably inserted through the indicator handle substantially near the club head end of the golf club shaft. The indicator handle functions to measure the flexure of the golf club shaft at differing angles when depressed downwardly as the golf club shaft is rotated.

20 Claims, 3 Drawing Sheets

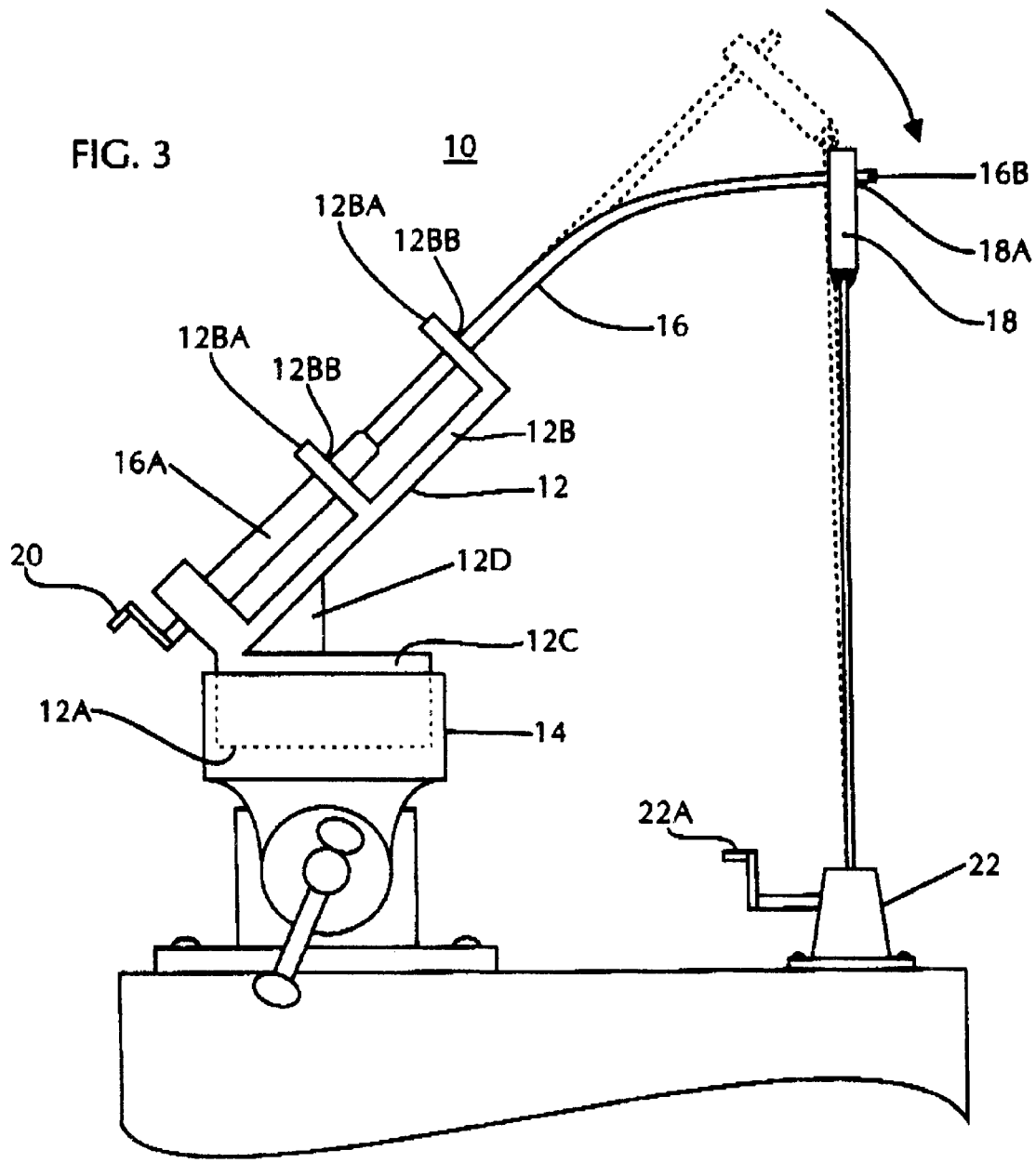

GOLF CLUB SPINE FINDER AND METHOD

BACKGROUND OF THE INVENTION

1. Field of the Invention

The present invention is a device designed to locate the spine, or strong side, of a golf club shaft. The device, in its preferred mode, comprises an indicator handle, a support structure, and the usage of a traditional vice means. A golf club shaft is held in place at one end by the vice, and extends through the support structure, which is equipped with roller bearings that function to allow the shaft to rotate on a vertical axis. The distal end of the shaft extends through the indicator handle, which is equipped with roller bearings as well. When tension is placed upon the distal end of the shaft in such a way as to bend the naturally flexing shaft downwardly, the indicator handle allows the user to locate the strongest and weakest points of the shaft. By using this information when affixing the club head onto the shaft in a precise manner, the device will increase the overall performance of the golf club.

2. Description of the Prior Art

Numerous innovations for golf club devices have been provided in the prior art that are described as follows. Even though these innovations may be suitable for the specific individual purposes to which they address, they differ from the present invention as hereinafter contrasted. The following is a summary of those prior art patents most relevant to the invention at hand, as well a description outlining the differences between the present invention and the prior art.

Patent #4,682,504, "Device For Measuring a Stiffness of a Golf Club Shaft," by Kobayashi, represents the closest prior art patent to the present invention. This patent describes a device for measuring a stiffness of a golf-club shaft comprises a clamp for holding one end of a golf-club shaft so that the golf-club shaft extends in a substantially horizontal position. A pointer member having a tip end and a root portion is detachably attached at the root portion thereof to the other end of the golf-club shaft held by the clamp so that the pointer member extends in a substantially horizontal position perpendicular to a longitudinal axis of the golf-club shaft. A counterweight is detachably attached to the tip end of the pointer member and applies a predetermined flexure and torsion load to the golf-club shaft through the pointer member. A vertical displacement measuring instrument is provided to measure the amount of vertical displacement of the tip end of the pointer member produced by torsion and flexure of the golf-club shaft when the predetermined load of the counterweight is applied to the golf-club shaft through the pointer member.

This prior art patent, however, differs from the present invention in significant respects. Firstly, the Kobayashi patent teaches the usage of a device that keeps the shaft of a golf club stationary while flexure of the club head end can be measured. This is accomplished by a clamping means, including the usage of bolts, securing the grip end of a golf club shaft in a horizontal position. Thus, unlike the present invention, the shaft can not be rotated about and flexure can not be measured at more than one angle selected.

Moreover, in the Kobayashi patent, flexure is measured by securing the grip end of the shaft in a housing and allowing the club head, already affixed on the shaft, to weigh down the distal end of the golf club when the club is fixed in its horizontal position. A vertical ruler-type piece then allows the user to calculate the curvature of the shaft. This secured-grip-end embodiment also allows the Kobayashi invention to measure the level of torsion of the club, or stress caused when one end of the club is twisted in one direction while the other is held motionless.

The present invention, in contrast, is aimed at production of golf clubs in the most effective manner possible. By using the present invention, unlike that of Kobayashi, one can determine the flexure of the shaft when the shaft is bent at any angle of rotation, prior to the club head being secured thereon. Therefore, the user of the present invention can locate the strongest and weakest points of the shaft and affix the club head to the shaft accordingly.

Finally, the present invention may be produced with either an analog or digital pressure indicator on the indicator handle for accurate reading of the curvature of the spine. In addition, the present invention can be produced to include a handle means removably attachable to the shaft for steady and convenient rotation of the shaft during operation.

Additional patents retrieved in a comprehensive search included. #3,992,933, Electromechanical Moment-Independent Deflection Sensor, #5,429,008, Method and Apparatus for Measuring Figure of Deflection of Golf Club Shaft, #4,558,863, Golf Club Shaft, #5,379,641, Method for Measuring the Deflection in the Shaft of a Golf Club for Controlling the Dynamic Loft Angle of a Club, #4,517,843, Material and Component Testing Machine, and #4,958,834, Golf Club Assembly.

SUMMARY OF THE INVENTION

The present invention is a device designed to locate the spine of a golf club shaft. The device, in its preferred mode, comprises an indicator handle, a support structure, and the usage of a traditional vice means. A golf club shaft held in place at one end by the vice, and extends through the support structure, which is equipped with roller bearings that function to allow the shaft to rotate on a vertical axis. The distal end of the shaft extends through the indicator handle, which is equipped with roller bearings as well. When tension is placed upon the distal end of the shaft in such a way as to bend the shaft downwardly, the indicator handle allows the user to locate the strongest and weakest points of the shaft. By using this information when affixing the club head onto the shaft in a precise manner, the device will increase the overall performance of the golf club.

More specifically, if the manufacturer of a golf club knew the strongest and weakest points of the club shaft, and hence the precise location of the spine, the manufacturer can align the club head with the strongest point of the shaft and affix the head onto the shaft accordingly. This will benefit the more powerful golfers who can generate significant force when swinging the club. Considering that the club head end is far more heavy than the grip end of the shaft, a golf club that does not have a properly aligned club head and spine may provide a weaker shot for the golfer, and may even break or be caused damage. More importantly, a club with a head that is not aligned with the spine or strong side of the shaft may twist on a horizontal axis, either during the swing itself or upon impact with the solid ground surface. By utilizing the present invention, the club maker can not only produce the most effective and strong club possible, but can produce a set of clubs fully consistent with one another in their flexure and performance.

The present invention solves the problems associated with golf clubs that are aligned improperly, as the location of the spine of the shaft can be easily ascertained, allowing the manufacturer to affix the golf club head to the shaft in the most optimal fashion. This can be accomplished quickly and relatively inexpensively, much to the advantage of the professional or amateur golfer.

The novel features which are considered characteristic for the invention are set forth in the appended claims. The invention itself, however, both as to its construction and its method of operation, together with additional objects and advantages thereof, will be best understood from the following description of the specific embodiments when read and understood in connection with the accompanying drawings.

BRIEF DESCRIPTION OF THE PREFERRED EMBODIMENT

FIG. 3 is a perspective view of the entirety of the golf club spine finder, including optional features therewith.

DETAILED DESCRIPTION OF THE PREFERRED EMBODIMENT

The foregoing will describe a golf club spine finder comprising a shaft holding means which comprises a bottom wall and a vertical member. The vertical member comprises a plurality of extended members, each extended member further comprising extended member apertures. A gripping means functions to secure the shaft holding means in a substantially upright position. A golf club shaft is then removably inserted through the extended member apertures of the shaft holding means, the golf club shaft comprising a traditional grip end and club head end. An indicator handle comprises at least one aperture further comprising roller bearings therein and display means. The golf club shaft is removably inserted through the indicator handle substantially near the club head end of the golf club shaft. The indicator handle functions to measure the flexure of the golf club shaft at differing angles when depressed downwardly as the golf club shaft is rotated.

Figure 1:
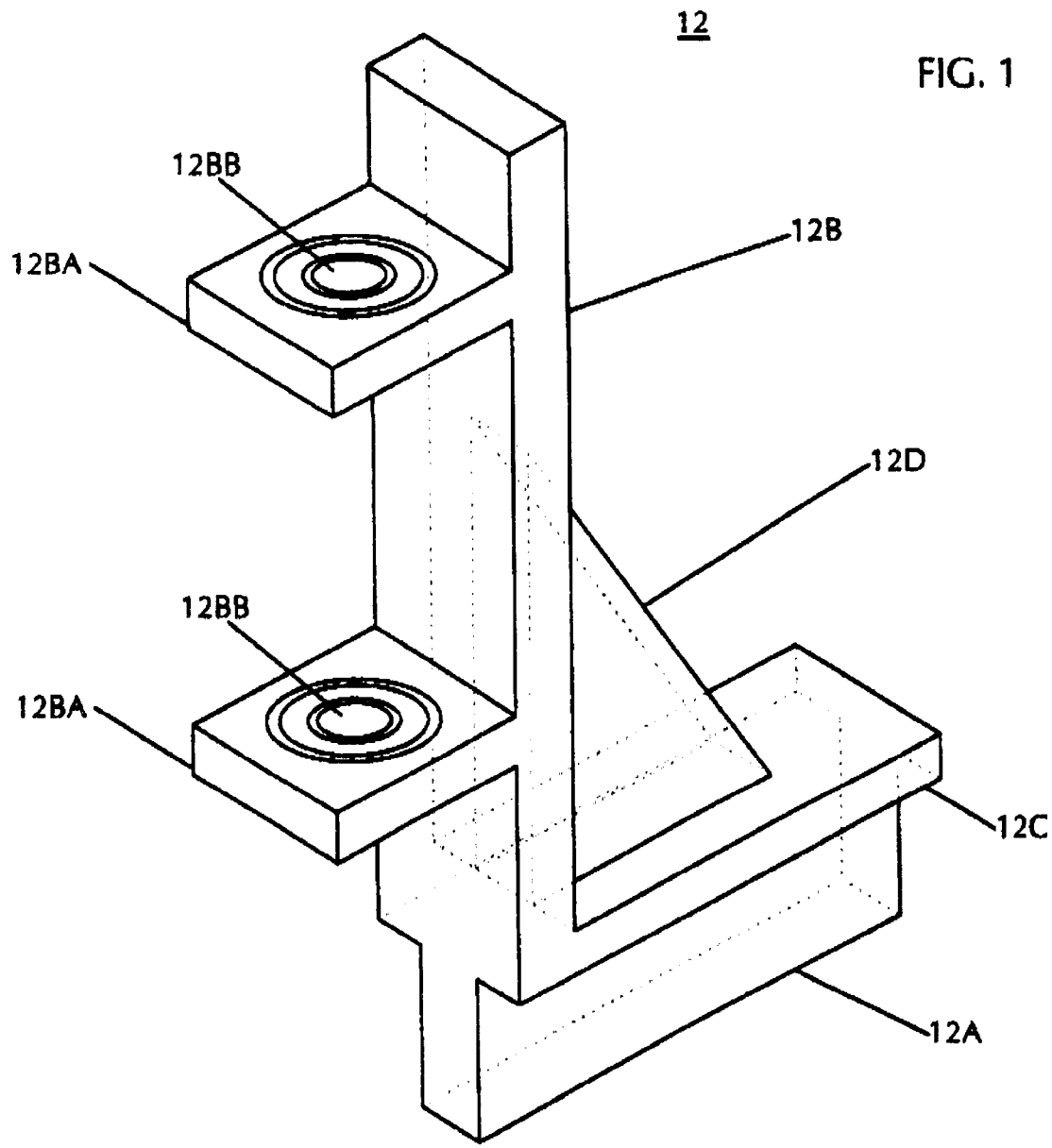
FIG. 1 is a perspective view of the shaft holding means of the golf club spine finder.

Firstly, referring to FIG. 1, which is a perspective view of the shaft holding means of the golf club spine finder: illustrated is a shaft holding means (12) which comprises a bottom wall (12A) and a vertical member (12B). The vertical member (12B) comprises a plurality of extended members (12BA), each extended member (12BA) further comprising extended member apertures (12BB). In addition, each extended member aperture (12BB) further comprises a plurality of roller bearings., which are designed to assist is rotating the shaft of a golf club that is inserted through the shaft holding means (12), providing little resistance thereto. Moreover, each extended member aperture (12BB) may alternatively include an aperture width adjustment means which functions to enlarge and reduce the size of the extended member aperture (12BB) allowing the extended member aperture (12BB) to substantially fit the contour of the golf club shaft (16). This is helpful as club shafts may be manufactured in a variety of widths and sized both differing than each other and varying or tapering within once such club shaft itself. Each extended member aperture (12BB) may also further comprise a cushioning means which functions to protect the golf club shaft (16) from damage during rotation thereof. This is particularly useful, as the club shaft may avoid being scratched during rotation against roller bearings or other such solid surfaces therein.

For increased stability, the shaft holding means (12) may further comprise a horizontal support member (12C) which functions to tightly secure the shaft holding means (12) to the gripping means (14). This horizontal support member (12C) may be a solid lip that is placed flush against an upper surface of the gripping device, preferably a traditional vice grip means. Similarly, the shaft holding means (12) may further comprise a shaft holding means angled support member (12D) which functions to tightly secure the shaft holding means (12) to the gripping means (14) and secure the golf club shaft (16) in a substantially upright position. The angled support member (12D) may be manufactured at a forty-five degree angle, or any other oblique angle that would act to bolster the stability of the shaft holding means (12), particularly in light of the fact that the user may be depressing, either manually or mechanically, significant downward pressure upon the golf club shaft at a position near the club head end of the shaft.

Figure 2:
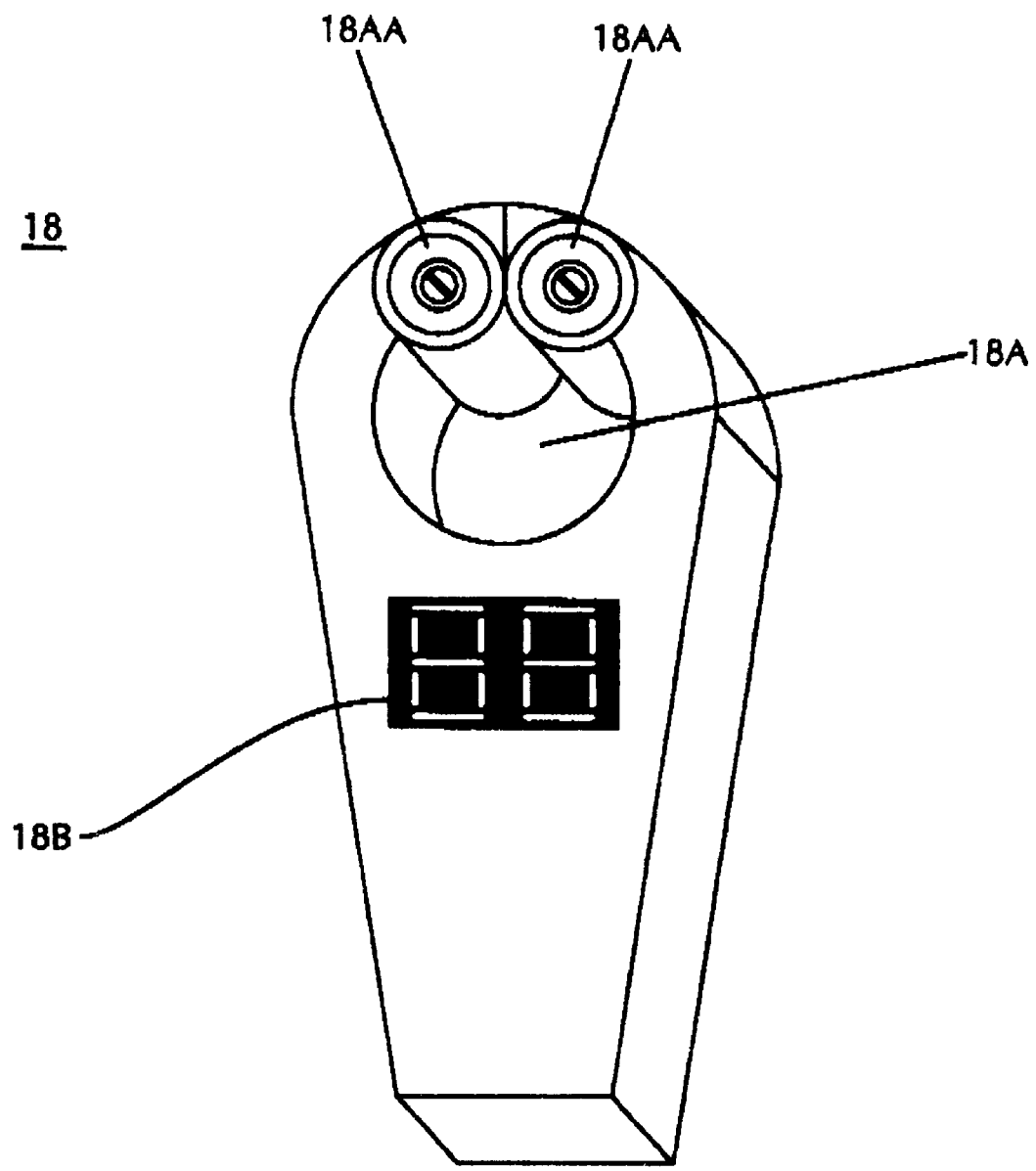
FIG. 2 is a perspective view of the indicator handle of the golf club spine finder.

Secondly, referring to FIG. 2, which is a perspective view of the indicator handle of the golf club spine finder: illustrated is an indicator handle (18) which comprises at least one indicator handle aperture (18A) and an indicator handle display means (18B). The indicator handle aperture (18A) further comprises roller bearings (18AA) therein, for the purpose of the golf club shaft (16) being removably inserted through the indicator handle (18) substantially near the club head end (16B) of the golf club shaft (16). The roller bearings function in a manner consistent with those similarly situated in the shaft holding means (12). The indicator handle (18) then functions to measure a flexure of the golf club shaft (16) at differing angles when depressed downwardly as the golf club shaft (16) is rotated. The principal object of the invention is that if the flexure of the shaft is measured at various points of rotation of said shaft, one can locate the spine of the shaft, or determine that point of rotation at which the greatest and least flexure of the shaft occur during downward pressure upon the indicator handle. The user or club maker can then utilize this information in affixing the club head onto the golf club shaft in the most effective means possible, such as by creating the strongest embodiment available.

The golf club spine finder (10) may alternatively further comprise an indicator handle anchoring means (22) which functions to removably secure the indicator handle (18) to a second structure during rotation of the golf club shaft (16). This indicator handle anchoring means (22) may further comprise an anchoring tension adjustment means (22A) which functions to allow a user to increase the flexure of the golf club shaft (16) during rotation thereof. As shown in the drawing, this anchoring tension adjustment means (22A) may be as simple as a crank mechanism which functions to shorten or lengthen a solid rope-like member connecting the indicator handle to a solid surface.

The indicator handle display means (18B), noted above, may include a display of pressure information that is analog or digital in nature. In addition, the indicator handle (18) may further comprise a central processing unit therein, the central processing unit functioning to process and record data relating to flexure of the golf club shaft (16). In a more advanced embodiment, this central processing unit may function to store and process data relating to flexure of a plurality of golf club shafts (16). Thus, the user of this embodiment is able to compare and contrast flexure information of several golf club shafts through the usage of traditional computer means, such as recordation in disk or hard drive form.

Thirdly, referring to FIG. 3, which is a perspective view of the entirety of the golf club spine finder, including optional features therewith: illustrated is a golf club spine finder (10) comprising: shaft holding means (12) which comprises a bottom wall (12A) and a vertical member (12B).

The vertical member (12B) comprises a plurality of extended members (12BA), each extended member (12BA) further comprising extended member apertures (12BB); a gripping means (14) which functions to secure the shaft holding means (12) in a substantially upright position; a golf club shaft (16) removably inserted through the extended member apertures (12BB) of the shaft holding means (12); the golf club shaft (16) comprising a grip end (16A) and club head end (16B); an indicator handle (18) which comprises at least one indicator handle aperture (18A) and an indicator handle display means (18B), the indicator handle aperture (18A) further comprising roller bearings (18AA), the golf club shaft (16) removably inserted through the indicator handle (18) substantially near the club head end (16B) of the golf club shaft (16), the indicator handle (18) functioning to measure a flexure of the golf club shaft (16) at differing angles when depressed downwardly as the golf club shaft (16) is rotated.

Furthermore, the golf club spine finder (10) may further comprise a rotation assisting means (20) which functions to allow a user to rotate the golf club shaft (16) upon a vertical axis as the indicator handle (18) is depressed downwardly. This rotation assisting means (20) may be by manual user operation, or may, alternatively be mechanical in nature. Another option is that the golf club spine finder (10) may further comprise a support stand which functions to allow the golf club spine finder (10) to be embodied in a single self-contained unit.

Lastly, described in the present invention is a method of locating a spine of a golf club shaft wherein a user performs the steps of: first securing a shaft holding means (12) to a gripping means (14). The shaft holding means (12) comprises a bottom wall (12A) and a vertical member (12B), the vertical member (12B) comprising a plurality of extended members (12BA), each extended member (12BA) further comprising extended member apertures (12BB). The gripping means (14) functions to secure the shaft holding means (12) in a substantially upright position.

Then, the user can removably insert a golf club shaft (16) through the extended member apertures (12BB) of the shaft holding means (12), the golf club shaft (16) comprising a traditional grip end (16A) and club head end (16B).

Next, the user can downwardly depress an indicator handle (18), the indicator handle (18) comprising at least one indicator handle aperture (18A) and an indicator handle display means (18B), the indicator handle aperture (18A) further comprising roller bearings (18AA). The golf club shaft (16) is removably inserted through the indicator handle (18) substantially near the club head end (16B) of the golf club shaft (16). The aforementioned downward depression of the indicator handle (18) functions to measure a flexure of the golf club shaft (16) at differing angles when depressed downwardly as the golf club shaft (16) is rotated.

The method described above may further include rotating the golf club shaft (16) upon a vertical axis by mechanical means as the indicator handle (18) is depressed downwardly. In addition, the method may include removably anchoring the indicator handle (18) to a second structure during rotation of the golf club shaft (16). This may aid in the convenience of the user as well as ensure a consistent and steady level of pressure placed upon the indicator handle (18) during operation. Finally, the method may further include adjusting the tension of the anchoring of the indicator handle (18) functioning to increase the flexure of the golf club shaft (16) during rotation thereof This option may assist the user in testing the club under differing conditions while still maintaining the consistent level of pressure placed downwardly upon the club head end of the shaft as described above.

It will be understood that each of the elements described above, or two or more together, may also find a useful application in other types of constructions differing from the type described above.

While the invention has been illustrated and described as embodied in a comer protection device, it is not intended to be limited to the details shown, since it will be understood that various omissions, modifications, substitutions and changes in the forms and details of the device illustrated and in its operation can be made by those skilled in the art without departing in any way from the spirit of the invention.

Without further analysis, the foregoing will so fully reveal the gist of the present invention that others can, by applying current knowledge, readily adapt it for various applications without omitting features that, from the standpoint of prior art, constitute essential characteristics of the generic or specific aspects of this invention.

What is claimed as new and desired to be protected by Letters Patent is set forth in the appended claims:

What is claimed is:

1. A golf club spine finder (10) comprising:
    A) shaft holding means (12) which comprises a bottom wall (12A) and a vertical member (12B), the vertical member (12B) comprising a plurality of extended members (12BA), each extended member (12BA) further comprising extended member apertures (12BB);
    B) a gripping means (14) which functions to secure the shaft holding means (12) in a substantially upright position;
    C) a golf club shaft (16) removably inserted through the extended member apertures (12BB) of the shaft holding means (12); the golf club shaft (16) comprising a grip end (16A) and club head end (16B);
    D) an indicator handle (18) which comprises at least one indicator handle aperture (18A) and an indicator handle display means (18B), the indicator handle aperture (18A) further comprising roller bearings (18AA), the golf club shaft (16) removably inserted through the indicator handle (18) substantially near the club head end (16B) of the golf club shaft (16), the indicator handle (18) functioning to measure a flexure of the golf club shaft (16) at differing angles when depressed downwardly as the golf club shaft (16) is rotated.

2. The golf club spine finder (10) as described in claim 1, wherein each extended member aperture (12BB) further comprises a plurality of roller bearings.

3. The golf club spine finder (10) as described in claim 1, wherein each extended member aperture (12BB) includes an aperture width adjustment means which functions to enlarge and reduce the size of the extended member aperture (12BB) allowing the extended member aperture (12BB) to substantially fit the contour of the golf club shaft (16).

4. The golf club spine finder (10) as described in claim 1, wherein each extended member aperture (12BB) further comprises a cushioning means which functions to protect the golf club shaft (16) from damage during rotation thereof.

5. The golf club spine finder (10) as described in claim 1, wherein the shaft holding means (12) further comprises a horizontal support member (12C) which functions to tightly secure the shaft holding means (12) to the gripping means (14).

6. The golf club spine finder (10) as described in claim 1, wherein the shaft holding means (12) further comprises a shaft holding means angled support member (12D) which functions to tightly secure the shaft holding means (12) to the gripping means (14) and secure the golf club shaft (16) in a substantially upright position.

7. The golf club spine finder (10) as described in claim 1, wherein the golf club spine finder (10) further comprises a rotation assisting means (20) which functions to allow a user to rotate the golf club shaft (16) upon a vertical axis as the indicator handle (18) is depressed downwardly.

8. The golf club spine finder (10) as described in claim 7, wherein the rotation assisting means (20) is manual user operation.

9. The golf club spine finder (10) as described in claim 7, wherein the rotation assisting means (20) is mechanical.

10. The golf club spine finder (10) as described in claim 1, wherein the golf club spine finder (10) further comprises an indicator handle anchoring means (22) which functions to removably secure the indicator handle (18) to a second structure during rotation of the golf club shaft (16).

11. The golf club spine finder (10) as described in claim 10, wherein the indicator handle anchoring means (22) further comprises an anchoring tension adjustment means (22A) which functions to allow a user to increase the flexure of the golf club shaft (16) during rotation thereof.

12. The golf club spine finder (10) as described in claim 1, wherein the indicator handle display means (18B) is analog.

13. The golf club spine finder (10) as described in claim 1, wherein the indicator handle display means (18B) is digital.

14. The golf club spine finder (10) as described in claim 1, wherein the golf club spine finder (10) further comprises a support stand which functions to allow the golf club spine finder (10) to be embodied in a single self-contained unit.

15. The golf club spine finder (10) as described in claim 1, wherein the indicator handle (18) further comprises a central processing unit therein, the central processing unit functioning to process and record data relating to flexure of the golf club shaft (16).

16. The golf club spine finder (10) as described in claim 15, wherein the central processing functions to store and process data relating to flexure of a plurality of golf club shafts (16).

17. A method of locating a spine of a golf club shaft wherein a user performs the steps of:
 A) securing a shaft holding means (12) to a gripping means (14), the shaft holding means (12) comprises a bottom wall (12A) and a vertical member (12B), the vertical member (12B) comprising a plurality of extended members (12BA), each extended member (12BA) further comprising extended member apertures (12BB); the gripping means (14) functioning to secure the shaft holding means (12) in a substantially upright position;
 B) removably inserting a golf club shaft (16) through the extended member apertures (12BB) of the shaft holding means (12), the golf club shaft (16) comprising a grip end (16A) and club head end (16B);
 C) downwardly depressing an indicator handle (18), the indicator handle (18) comprising at least one indicator handle aperture (18A) and an indicator handle display means (18B), the indicator handle aperture (18A) further comprising roller bearings (18AA), the golf club shaft (16) removably inserted through the indicator handle (18) substantially near the club head end (16B) of the golf club shaft (16), downward depression of the indicator handle (18) functioning to measure a flexure of the golf club shaft (16) at differing angles when depressed downwardly as the golf club shaft (16) is rotated.

18. The method of locating a spine of a golf club shaft as described in claim 17, wherein the method further includes rotating the golf club shaft (16) upon a vertical axis by mechanical means as the indicator handle (18) is depressed downwardly.

19. The method of locating a spine of a golf club shaft as described in claim 17, wherein the method further includes removably anchoring the indicator handle (18) to a second structure during rotation of the golf club shaft (16).

20. The method of locating a spine of a golf club shaft as described in claim 17, wherein the method further includes adjusting the tension of the anchoring of the indicator handle (18) functioning to increase the flexure of the golf club shaft (16) during rotation thereof.

* * * * *